(12) United States Patent
Sunshine et al.

(10) Patent No.: US 6,996,478 B2
(45) Date of Patent: Feb. 7, 2006

(54) MULTIPLE SENSING SYSTEM AND DEVICE

(75) Inventors: Steven A. Sunshine, Pasadena, CA (US); M. Gregory Steinthal, Los Angeles, CA (US); Ajoy Roy, Pasadena, CA (US)

(73) Assignee: Smiths Detection Inc., Pasadena, CA (US)

( * ) Notice: Subject to any disclaimer, the term of this patent is extended or adjusted under 35 U.S.C. 154(b) by 7 days.

(21) Appl. No.: 10/799,185

(22) Filed: Mar. 11, 2004

(65) Prior Publication Data

US 2004/0181346 A1 Sep. 16, 2004

Related U.S. Application Data

(63) Continuation of application No. 09/596,169, filed on Jun. 16, 2000, now Pat. No. 6,839,636, which is a continuation of application No. 09/518,179, filed on Mar. 2, 2000.

(60) Provisional application No. 60/139,842, filed on Jun. 17, 1999.

(51) Int. Cl.
*G01N 33/497* (2006.01)

(52) U.S. Cl. ............................ 702/22; 702/23; 702/24; 702/30; 702/31; 702/32; 73/23.34

(58) Field of Classification Search .................. 702/136, 702/22–24, 27, 28, 30–36, 40, 56, 57, 64, 702/65, 81–84, 99, 104, 113–119, 124, 126, 702/130, 132–134, 138, 183, 184, 189; 73/39, 73/38, 23.21, 61.59, 61.61, 866, 866.2, 23.24, 73/23.2, 31.06, 31.05; 422/82.01, 68.1, 82.02, 422/8, 90, 98; 204/422, 424, 452, 431, 432, 204/400, 412, 406; 436/149, 150, 151
See application file for complete search history.

(56) References Cited

U.S. PATENT DOCUMENTS

| | | | |
|---|---|---|---|
| 1,455,263 A | 5/1923 | Oberfell |
| 2,743,167 A | 4/1956 | Cherry |
| 3,266,293 A | 8/1966 | Hubner |
| 3,323,350 A | 6/1967 | Roberts |
| 3,415,108 A | 12/1968 | Hubner |
| 3,427,862 A | 2/1969 | Hubner |
| 3,529,459 A | 9/1970 | Vilinstras |
| 3,540,261 A | 11/1970 | Scoggins |

(Continued)

FOREIGN PATENT DOCUMENTS

| | | |
|---|---|---|
| DE | 3615876 A1 | 11/1987 |
| DE | 196 36 461 A1 | 3/1998 |
| DE | 197 04 237 A1 | 8/1998 |
| WO | WO 92/22813 | 12/1992 |

OTHER PUBLICATIONS

Ulmer, H., et al., "Odours and flavours Identified with hybrid modular sensor systems", Sensors and Actuators B, 43: 24–33 (1997).

(Continued)

*Primary Examiner*—Carol S. W. Tsai
(74) *Attorney, Agent, or Firm*—Foley & Lardner LLP

(57) ABSTRACT

The present invention provides a distributed sensing system in a networked environment for identifying an analyte, including a first sensor array connected to the network comprising sensors capable of producing a first response in the presence of a chemical stimulus; a second sensor array connected to the network comprising sensors capable of producing a second response in the presence of a physical stimulus; and a computer comprising a resident algorithm. The algorithm indicates or selects the most relevant sensor in the network to identify the analyte. The sensors can be separated over large spatial areas, wherein the sensor arrays are networked. Suitable networks include a computer local area network, an intranet or the Internet.

14 Claims, 9 Drawing Sheets

U.S. PATENT DOCUMENTS

| | | |
|---|---|---|
| 4,329,870 A | 5/1982 | Farmer |
| 4,360,856 A | 11/1982 | Witthaus |
| 4,670,405 A | 6/1987 | Stetter et al. |
| 4,759,210 A | 7/1988 | Wohltjen |
| 4,762,594 A * | 8/1988 | Guruswamy ............... 205/792 |
| 4,779,451 A | 10/1988 | Ezawa et al. |
| 4,818,348 A | 4/1989 | Stetter |
| 4,864,492 A | 9/1989 | Blakely-Fogel et al. |
| 4,907,441 A | 3/1990 | Shurmer |
| 4,922,669 A | 5/1990 | De Pas et al. |
| 4,933,669 A | 6/1990 | Lyons |
| 5,025,653 A | 6/1991 | Schuldt |
| 5,029,300 A | 7/1991 | Ishibashi et al. |
| 5,304,495 A | 4/1994 | Yim |
| 5,309,777 A | 5/1994 | Schmitt et al. |
| 5,377,528 A | 1/1995 | Dauvergne |
| 5,435,176 A * | 7/1995 | Manchak, III ............ 73/152.43 |
| 5,469,369 A | 11/1995 | Rose-Pehrsson et al. |
| 5,541,851 A * | 7/1996 | Sato et al. .................. 700/266 |
| 5,571,401 A | 11/1996 | Lewis et al. |
| 5,571,947 A | 11/1996 | Senn et al. |
| 5,582,797 A | 12/1996 | Kewley et al. |
| 5,585,575 A | 12/1996 | Corrigan et al. |
| 5,654,497 A | 8/1997 | Hoffheins et al. |
| 5,675,070 A | 10/1997 | Gelperin |
| 5,677,476 A | 10/1997 | McCarthy et al. |
| 5,710,722 A | 1/1998 | Wood |
| 5,719,325 A | 2/1998 | Kiesele et al. |
| 5,728,581 A | 3/1998 | Schwarz et al. |
| 5,801,297 A | 9/1998 | Mifsud et al. |
| 5,808,541 A | 9/1998 | Golden |
| 5,811,812 A | 9/1998 | Williams et al. |
| 5,828,851 A | 10/1998 | Nixon et al. |
| 5,832,411 A | 11/1998 | Schatzmann et al. |
| 5,834,626 A | 11/1998 | DeCastro et al. |
| 5,891,398 A | 4/1999 | Lewis et al. |
| 5,892,950 A | 4/1999 | Rigori et al. |
| 5,911,872 A | 6/1999 | Lewis et al. |
| 5,931,913 A | 8/1999 | Meriwether et al. |
| 5,951,846 A | 9/1999 | Lewis et al. |
| 5,959,191 A | 9/1999 | Lewis et al. |
| 5,984,023 A * | 11/1999 | Sharma et al. ............... 175/50 |
| 6,003,620 A * | 12/1999 | Sharma et al. ............... 175/50 |
| 6,010,616 A | 1/2000 | Lewis et al. |
| 6,013,229 A | 1/2000 | Lewis et al. |
| 6,017,440 A | 1/2000 | Lewis et al. |
| 6,049,283 A | 4/2000 | Lindsray |
| 6,052,737 A | 4/2000 | Bitton et al. |
| 6,061,753 A | 5/2000 | Ericson |
| 6,085,576 A | 7/2000 | Sunshine et al. |
| 6,093,308 A | 7/2000 | Lewis et al. |
| 6,148,280 A | 11/2000 | Kramer |
| 6,169,775 B1 | 1/2001 | Takahashi et al. |
| 6,170,318 B1 * | 1/2001 | Lewis ...................... 73/23.34 |
| 6,182,497 B1 | 2/2001 | Krajci |
| 6,182,499 B1 | 2/2001 | McFarland et al. |
| 6,196,057 B1 | 3/2001 | Discenzo |
| 6,220,371 B1 | 4/2001 | Sharma et al. |
| 6,244,096 B1 | 6/2001 | Lewis et al. |
| 6,252,510 B1 * | 6/2001 | Dungan ..................... 340/632 |
| 6,331,244 B1 | 12/2001 | Lewis et al. |
| 6,350,369 B1 | 2/2002 | Lewis et al. |
| 6,387,329 B1 | 5/2002 | Lewis et al. |
| 6,627,154 B1 * | 9/2003 | Goodman et al. ........ 422/82.01 |
| 2002/0005580 A1 | 1/2002 | Lewis et al. |
| 2002/0028456 A1 | 3/2002 | Mansky et al. |
| 2002/0137084 A1 | 9/2002 | Quate et al. |
| 2002/0141901 A1 | 10/2002 | Lewis et al. |
| 2002/0192117 A1 * | 12/2002 | Lewis et al. ............. 422/82.05 |
| 2004/0088113 A1 * | 5/2004 | Spoonhower et al. .......... 702/2 |
| 2005/0061056 A1 * | 3/2005 | Sunshine et al. ............ 73/23.2 |

OTHER PUBLICATIONS

Winquist, F., et al., "The combination of an electronic tongue and an electronic nose", Sensors and Actuators B, 58: 512–517 (1999).

Gardner et al., "Detection of vapours and odours from a multisensor array using pattern–recognition techniques", Sensors and Actuators B., 9:9–15 (1992).

Supplementary European Search Report for EP 0 94 1511 dated Jul. 3, 2002.

International Search Report for PCT/US00/05585 completed Jun. 30, 2000.

* cited by examiner

Sensor Array
(2 Chips)

IR/Polymer-Based Sensor

Section View: Sensor Chamber

MULTIPLE SENSING SYSTEM AND DEVICE

CROSS-REFERENCES TO RELATED APPLICATIONS

This application is a continuation of U.S. application Ser. No. 09/596,169 filed Jun. 16, 2000, which is now U.S. Pat. No. 6,839,636, which is a continuation of U.S. application Ser. No. 09/518,179, filed Mar. 2, 2000, which claims the benefit under 35 U.S.C. §119(e) of U.S. Provisional Application Ser. No. 60/139,842, filed Jun. 17, 1999, the teachings of each of which are incorporated herein by reference in their entireties for all purposes.

FIELD OF THE INVENTION

In general, this invention relates to a multiple sensing modalities and, in particular, a system, device and method that comprises sensors capable of detecting a combination of chemical stimuli and physical stimuli.

BACKGROUND OF THE INVENTION

An electronic nose or artificial olfactory system is a device that is capable of detecting a wide variety of analytes in fluids such as vapors, gases and liquids. The device comprises an array of sensors that in the presence of an analyte produces a response, such as an electrical response. The device produces a unique signature output for a particular analyte. Using pattern recognition algorithms, the output signature can be correlated and compared to a particular analyte or mixture of substances that are known. By comparing the unknown signature with the stored or known signatures the analyte can be identified.

Current commercially available sensors can be used for a variety of applications. These commercial applications include, but are not limited to, environmental toxicology and remediation, biomedicine, such as microorganism classification or detection, material quality control, food and agricultural products monitoring, heavy industrial manufacturing, ambient air monitoring, worker protection, emissions control, and product quality testing.

Although in some instances, an electronic nose is sufficient to accurately determine the analyte of interest, other physical data within the environment of the analyte go undetected. These additional data can be used to identify the analyte. Physical parameters of the analyte include, but are not limited to, temperature, humidity, color, pH, solution concentration, wavelength absorption, taste, vapor pressure, mass, pressure, optical density, magnetic field, etc. By measuring these physical parameters in conjunction with electronic nose data, a more accurate assessment of the analyte and its surrounding environment can be accomplished.

For example, the current state of the art breathalyzer used to determine the blood alcohol content includes an infrared detector (IR). In certain instances, IR detectors are susceptible to interferences from other volatile organic compounds (VOC) which also absorb the IR, (see, Jones A W, *J. Anal Tox*. 20:522–527 (1996)). Manufacturers of these evidentiary instruments have responded by adding additional channels in an effort to differentiate between the IR signature of ethanol and other volatile organic compounds. These volatile organic compounds include acetone, toluene, xylene, methanol, isopropanol, and acetaldehyde, the list also includes water, carbon monoxide and carbon dioxide. Concentrations of the other analytes in the test gas are generally in the range of 0.01 to 0.10 mg/L. However, these modification are still ineffectual.

Hybrid sensor systems containing different types of chemical sensors are known. For example, a system known as the MOSES system exists wherein a modular system was used that included an array of different semiconducting gas sensors based on metal oxides, polymer coated quartz microbalance sensors, calorimetric sensors and electrochemical sensors. The MOSES system optionally contained a semiconductor field effect transistor sensor (MOSFET). The system is limited to detecting odors using chemical sensors (see, H. Ulmer et al., *Sensors and Actuators B*, 43, 24–33 (1997)).

In addition, U.S. Pat. No. 5,801,297, which issued to Mifsud et al., on Sep. 1, 1998, also discloses a hybrid chemical sensor system. This system includes a first enclosure having a first detection means wherein the first detection comprises a plurality of gas sensors using a same first technology selected from semiconductor gas sensors technology, conductive polymer gas sensors technology, or acoustic surface wave gas sensors technology. The system also includes a second enclosure having a second detection means. The second detection means includes a plurality of gas sensors using a same second technology selected from semiconductor gas sensors technology, conductive polymer gas sensors technology, or acoustic surface wave gas sensors technology. In this system, the second technology is different from the first technology.

In another hybrid sensor system, a combination of an electronic tongue and an electronic nose is described. In this system, the electronic nose consisted of an array of gas sensors with pattern signal handling capability and sensor pattern recognition algorithms. The electronic tongue consisted of taste analysis of liquids based upon pulsed voltammetry. (see, F. Winquist et al., *Sensors and Actuators B* 58, 512–217 (1999).

Moreover, U.S. Pat. No. 5,832,411, which is issued to Schatzmann, et al., on Nov. 3, 1998, discloses a plurality of sensor units distributed over an area that communicate via a network with a central monitoring unit. The sensor units include sensor arrays that provide them with raw data in response to the presence of selected compounds in the ambient fluid. The raw sensor data is then processed to compute a local profile. The local profiles from the individual sensor units are then used to compute a spatial and temporal map for the compounds in the fluid. This map can then be used for a variety of purposes including tracking and predicting the flow of compounds through the area, identifying the source of compounds in the area, monitoring abatement, and controlling industrial processes.

In view of the foregoing, what is needed in the art is a system that can capture both physical data and chemical data in a particular environment, especially a networked environment. A system is needed which can respond to a combination of a chemical stimulus and a physical stimulus. The responses can be stored and analyzed and thereby identify the analyte of interest. The current invention fulfills these and other needs.

SUMMARY OF THE INVENTION

Commercial artificial olfactory systems are widely used by industry to provide quality control of products such as wine, beer, coffee, and cheese. These systems are limited as they only detect chemical aromas and vapors by chemical means. Other physical parameters and stimuli of the analyte go undetected. By detecting both chemical stimuli and physical stimuli an analyte and its environment can be assessed and identified more accurately.

As such, in certain embodiments, the present invention provides a distributed sensing system in a networked environment for identifying an analyte, the system comprising: a first sensor array connected to the network comprising sensors capable of producing a first response in the presence of a chemical stimulus; a second sensor array connected to the network comprising sensors capable of producing a second response in the presence of a physical stimulus; and a computer comprising a resident algorithm to process the responses and identify the analyte. In a preferred embodiment, the algorithm indicates or selects the most relevant sensor in the network to identify the analyte. The algorithm selects the most relevant sensor modality to use within each sensor array for a particular application. In this embodiment, the sensors can be separated over large spatial areas, wherein the sensor arrays are networked. Suitable networks include a computer local area network, an intranet or the Internet.

Various sensor types and combinations thereof comprise the first sensor array. Sensors capable of detecting a chemical stimuli and suitable for use in the present invention include, but are not limited to, bulk conducting polymer films, semiconducting polymer sensors, surface acoustic wave devices, fiber optic micromirrors, quartz crystal microbalances, conducting/nonconducting regions sensors and dye impregnated polymeric coatings on optical fibers.

Similarly, a wide range of physical stimuli can be detected using the second sensor array of the present invention. These sensors include, but are not limited to, optical sensors, mechanical sensors, radiation sensors, thermal sensors and combinations thereof. In a preferred aspect, the physical stimulus is detected using an optical sensor. Optical stimuli can be measured as wave amplitude, phase, polarization, wave velocity, refractive index, emissivity, reflectivity and absorption. In a preferred aspect, the second sensor array comprises an IR sensor. The IR sensor comprises an IR source to provide IR radiation through a gas sample contained in a sample cell for detection by a detector. In this sensor, the amplitude of the signal detected by the detector at a particular wavelength, which corresponds to the absorption wavelength of a gas of interest, provides an indication of the concentration of that gas in the sample. Various filters can be used with the infrared sensors that are specific for various analytes. In order to detect ethanol for example, a 3.46 $\mu$m filter is used. If the analyte absorbs at this frequency, ethanol may be present. The absorption can then be confirmed using the sensors that detect the chemical stimulus.

In another embodiment, the present invention relates to a device for monitoring an analyte in an environment. In this aspect, the device comprises at least one sensor array, wherein the array of sensors comprises at least two sensors capable of producing a first response in the presence of a chemical stimulus; a second sensor capable of producing a second response in the presence of a physical stimulus; a connector that connects each of the sensors comprising the at least one sensor array and the second sensor to a central processing unit that collects and stores the first and the second responses; and an analyzer configured to analyze the first and second responses. The analyzer monitors the analytes in the environment. As used herein, the term "monitor" refers to detection, identification, quantification, classification or combinations thereof. Preferably, the second sensor is an array of sensors. The device can be a handheld device.

In a preferred embodiment, chemical stimuli are detected using sensors that are disclosed in U.S. Pat. No. 5,571,401, which issued to Lewis et al., on Nov. 5, 1996, and is incorporated herein by reference in its entirety for all purposes. The sensors described therein are conducting materials and nonconducting materials arranged in a matrix of conducting and nonconducting regions. The nonconductive material can be a nonconducting polymer such as polystyrene. The conductive material can be a conducting polymer, carbon black, an inorganic conductor and the like. The sensor arrays comprise at least two sensors, typically about 32 sensors, and in certain instances 1000 or more sensors.

In yet another embodiment, the present invention provides a method of for transferring a combination of chemical and physical data over a computer network for identification of an analyte. The method includes transmitting sensory data from a first sensor array comprising sensors capable of producing a first response in the presence of a chemical stimulus to a remote location; transmitting physical data from a second sensor array comprising sensors capable of producing a second response in the presence of a physical stimulus to a remote location; and processing the sensory and physical data at the remote location for identification of an analyte.

Numerous advantages are achieved using the present invention over conventional systems. For example, the present system captures additional stimuli that in traditional sensing systems goes undetected. This feature allows unparalleled detection and identification of analytes in an environment. By detecting additional stimuli in the environment, a more robust system is realized. In addition, because the system comprises multiple modalities of sensors, fewer incorrect identifications are made.

The foregoing embodiments as well as other features and advantages of the present invention will be more apparent when read with the accompanying drawings and detailed description which follows.

DETAILED DESCRIPTION OF THE INVENTION AND PREFERRED EMBODIMENTS

I. System

Although electronic noses are commercially available, they are limited to the detection of chemical stimuli such as odors, vapors, fluids and gases. The present invention provides a multiple sensing apparatus that is capable of responding to a variety of stimuli that is both chemical and physical in nature. By sensing both chemical and physical stimuli, a more accurate detection or identification of the environment and unknown analyte can be accomplished.

Figure 1:
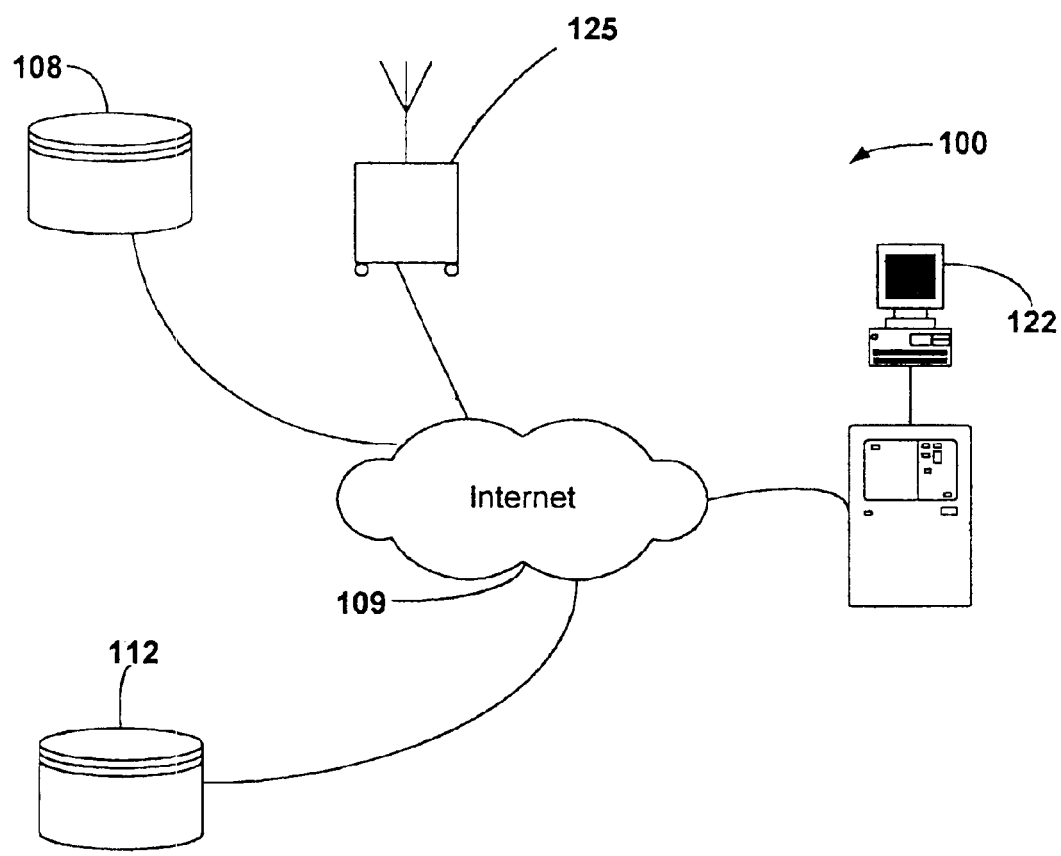
FIG. 1 shows an embodiment of a networked environment of the present invention.

In one embodiment, the systems of the present invention can operate in a networked environment. FIG. 1 represents one environment in which the systems of present invention can be used. This diagram is merely an illustration and should not limit the scope of the claims herein. One of ordinary skill in the art will recognize other variations, modifications, and alternatives.

The distributed sensing system 100 includes a network 109 such as, for example, the Internet. The distributed sensing system 100 includes a first sensor array 108 connected to the network comprising sensors capable of producing a first response in the presence of a chemical stimulus; a second sensor array 112 connected to the network comprising sensors capable of producing a second response in the presence of a physical stimulus; and a computer 122 comprising a resident algorithm. In a preferred aspect, the algorithm indicates or selects the most relevant sensor modality in the network to identify an analyte.

The network allows for communication of each of the sensors, such as a mobile sensor unit 125, to the central processing unit or computer. A number of different technologies can be used to implement the communications between the first array of sensors 108, the second array of sensors 112, and the computer comprising a resident algorithm.

In order to provide transmission of captured analyte stimuli, the first and second sensor array includes a communication interface that is capable of being coupled to the computer network 109. Suitable communication interfaces include, but are not limited to, an Ethernet interface, an RS-232 interface, a parallel port, a universal serial bus (USB), an infrared data link, an optical interface and a RF interface. Alternatively, in some aspects, the sensor arrays can be hard wired directly to the network.

The computer network 109 can be one of a variety of networks including a worldwide computer network, an internet, the Internet, a WAN, a LAN or an intranet. It should be understood that access to the computer network is conducted through a gateway. A gateway is a machine, for example, a computer that has a communication address recognizable by the computer network.

In certain embodiments, the sensor array can communicate with the computer network 109 via the communication interface using either wireless 125 or wired technologies. Wireless technologies can include infrared, radio waves, satellite and microwaves. In certain aspects, the sensor arrays have wireless Ethernet capabilities such as a radio-card having a media access controller. In certain aspects, the media access controller regulates the data from the sensor array to the network.

In one embodiment, the system of the present invention includes a first array of sensors wherein the sensors detect a chemical stimulus. Suitable chemical stimuli capable of detection include, but are not limited to, analytes in fluids such as a vapor, a gas, a liquid, a solid, an odor or mixtures thereof. This aspect of the device comprises an electronic nose. Suitable sensors comprising the first array of sensors include, but are not limited to, bulk conducting polymer films, semiconducting polymer sensors, surface acoustic wave devices, fiber optic micromirrors, quartz crystal microbalances, conducting/nonconducting regions sensors and dye impregnated polymeric coatings on optical fibers and combinations thereof. In one especially preferred aspect, the electronic nose comprises conducting/nonconducting regions sensors. It will be apparent to those of skill in the art that the electronic nose array can comprise combinations of the foregoing sensors.

The present invention relates to a system that is capable of measuring or detecting both physical and chemical parameters. In this manner, a more robust and rigorous analysis of the environment can be accomplished with a more accurate determination of the identity of the unknown analyte. Thus, in one embodiment, the system comprises a second array of sensors that are capable of detecting a wide range of physical stimuli. These sensors include, but are not limited to, optical sensors, mechanical sensors, radiation sensors, thermal sensors and combinations thereof. In a preferred aspect, the physical stimulus is detected using an optical sensor. Optical stimuli can be expressed as wave amplitude, phase, polarization, wave velocity, refractive index, emissivity, reflectivity and absorption. In a preferred aspect, the second sensor array comprises an IR sensor.

Concentration of gases, such as CO, $CO_2$, hydrocarbons (e.g. $CH_4$), carboxylic acids, microorganism off-gases or metabolites, ketones, alcohols, anesthetic agent gases, exhaust gases, Freon, or other gases can be determined by IR radiation. Each species of gas typically has one or more distinct IR absorption characteristics and better absorbs IR radiation at or near a particular wavelength. The absorption of IR radiation at a frequency corresponding to a characteristic absorption wavelength of a particular gas species is directly related to the concentration of that species in the gas sample. Thus, the amplitude of the signal detected by the IR detector at a wavelength corresponding to a characteristic absorption wavelength of a particular gas species is inversely proportional to the concentration of that species in the gas sample.

The distributed sensing system 100 can be used in many different applications. For example, the sensor units can be distributed across an oil refinery to monitor the leakage of volatile gases into the atmosphere. A valve failure, for example, will be discovered immediately and a technician dispatched before it can present a serious safety hazard or seriously impact the operation of the refinery. In this embodiment, the technician can have a handheld sensing device as described in WO 99/47905, published Sep. 23, 1999, and incorporated herein by reference. At the scene of the leak, the technician can assess the amount and nature of the leak. The handheld device can communicate with the network via wireless mode.

The system can also be used to monitor emission levels from industrial plants such as chemical or textile facilities. The data gathered can then be used to track and predict the progression of a plume of escaped dangerous or poisonous gas. In cases of an industrial incident, this information can be used to first warn downwind populations and later to estimate the impact of the incident on those environments. In many industrial facilities, such as a nuclear facility, the sensor system can be used to monitor the perimeter. In incineration plants that produce dangerous compounds, the processes that are used to destroy compounds can be monitored.

The system of the present invention can be used in myriad other applications in addition to the foregoing. These applications include, but are not limited to, environmental toxicology and remediation, biomedicine, materials quality control, food and agricultural products monitoring. Further applications include: heavy industrial manufacturing (automotive, aircraft, etc.), such as ambient air monitoring, worker protection, emissions control, and product quality testing; oil/gas petrochemical applications, such as combustible gas detection, $H_2S$ monitoring, and hazardous leak detection and identification; emergency response and law enforcement applications, such as illegal substance detection and identification, arson investigation, hazardous spill identification, enclosed space surveying, and explosives detection; utility and power applications, such as emissions monitoring and transformer fault detection; food/beverage/agriculture applications, such as freshness detection, fruit ripening control, fermentation process monitoring and control, flavor composition and identification, product quality and identification, and refrigerant and fumigant detection.

Additional applications include, but are not limited to, cosmetic/perfume applications, such as fragrance formulation, product quality testing, and fingerprinting; chemical/plastics/pharmaceuticals applications, such as fugitive emission identification, leak detection, solvent recovery effectiveness, perimeter monitoring, and product quality testing; hazardous waste site applications, such as fugitive emission detection and identification, leak detection and identification, transportation applications, such as hazardous spill monitoring, refueling operations, shipping container inspection, and diesel/gasoline/aviation fuel identification; building/residential applications, such as natural gas detection, formaldehyde detection, smoke detection, automatic ventilation control (cooking, smoking, etc.), and air intake monitoring; hospital/medical applications, such as anesthesia and sterilization gas detection, infectious disease detection, breath, wound and body fluids analysis, and telesurgey.

Terminal 122 is connected to a server. This connection can be by a network such as Ethernet, asynchronous transfer mode, IEEE standard 1553 bus, modem connection, universal serial bus, etc. The communication link need not be a wire but can be infrared, radio wave transmission, etc. The server is coupled to the Internet 109. The Internet is shown symbolically as a cloud or a collection of server routers 109. The connection to server to the Internet is typically by a relatively high bandwidth transmission medium such as a T1 or T3 line.

Figure 2:
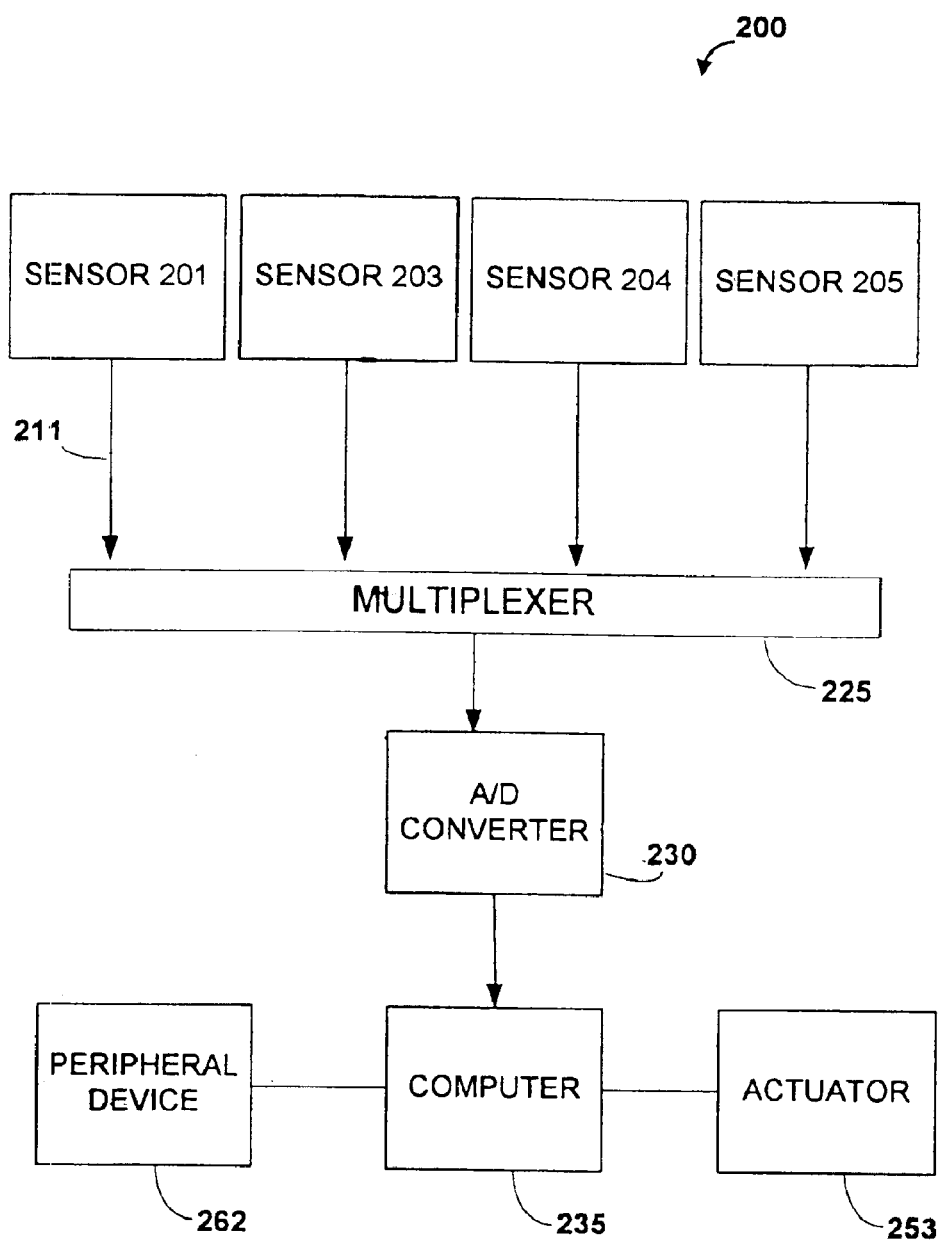
FIG. 2 shows a distributed sensing environment of the present invention.

FIG. 2 represents one embodiment of a system of the present invention. This diagram is merely an illustration and should not limit the scope of the claims herein. One of ordinary skill in the art will recognize other variations, modifications, and alternatives.

FIG. 2 is a block diagram 200 of a system of the present invention. In this environment, such as a hospital setting, data are collected from a patient from a number of sensor arrays 201, 203, 204 and 205. The sensor arrays can be positioned directly on an object such as a hospital bed, or inside, or on the patient (such as a thermometer). In this embodiment, sensor 201 is a chemical sensor array for detecting the patient's breath. Using the breath sample, the patient's well being can be monitored. Sensor 203 is a noncontact sensor, such as a video monitor. Sensor 204 is an array of thermistors that are temperature sensitive resistors that monitors the patient's temperature (such as oral and anal cavities). Sensor 205 is an optical sensor, such as an IR sensor that will allow more accurate identification of the patient's breath.

In order to provide transmission of captured analyte stimuli, e.g., breath and temperature, the first and second sensor array includes a communication interface 211 that is capable of being coupled to the computer network. Electrical signals from the sensors are thereafter fed into a multiplexer 225 that functions to connect the sensor arrays one at a time to an analog-to-digital (A/D) converter 230 or directly to a computer 235. The computer 235 controls a multiplexer 225 and an A/D converter 230 for the appropriate timing.

In another embodiment, the computer is connected via the network to an array of actuators 253 that interact with various accessory devices. These actuators can employ alarm signals, pneumatic valves for dispensing pharmaceuticals, etc. The system optionally comprises peripheral devices 262, including, but not limited to, a data recorder, a display, a monitor, etc.

In operation, the system of the present invention is more accurate at identifying an analyte than a single array alone. For instance, in the case of diabetics and persons who have abstained from food for a long period of time, acetone can appear in the blood and enter the alveoli of the lungs and eventually the breath. In addition, a person who has consumed ethanol will have ethanol present in their breath. Acetone and alcohol both have hydrocarbon absorptions, i.e., the 3.34 µm band in the infrared spectrum. However, when the IR sensors are used in conjunction with the chemical sensors, the chemical sensor array gives confirmation that the hydrocarbon present is either alcohol or ethanol. Thus, a tandem sensor array approach of detecting analytes gives a more accurate assessment of the analyte of interest.

Using the present system, it is possible to monitor a patient health and well-being. For example, WO 98/29563, published Jul. 9, 1998, and incorporated herein by reference, discloses a method for monitoring conditions in a patient wherein a sample is obtained from a patient over a period of time. The samples are then flowed over a gas sensor and a response is measured. Thereafter, the response is correlated with known responses for known conditions. The conditions include, but are not limited to, the progression and/or regression of a disease state, bacterial infections, viral, fungal or parasitic infections, the effectiveness of a course of treatment and the progress of a healing process.

In another embodiment, the system of the present invention can be used to monitor other medical conditions as set forth in WO 99/13786, which published on Dec. 23, 1999, and is incorporated herein by reference. As disclosed therein, volatile marker gases characterize the detection or diagnosis of a disease state or medical condition. The methods and apparatus can advantageously by used to detect volatile marker gases and compounds indicative of medical conditions, disease processes, infections, illness and well-being. Using these marker gases and compounds, clinicians can use the diagnostic instruments and the systems, devices methods of the present invention to make diagnoses and formulate appropriate treatments. Various marker gases include, but are not limited to, alkanes, alkenes, alkynes, dienes, alicyclic hydrocarbons, arenes, alcohols, ethers, ketones, aldehydes, carbonyls, carbanions, polynuclear aromatics, biomolecules, sugars, isoprenes isoprenoids, VOC, VOA, indoles, skatoles, diamines, pyridines, picolines, an off-gas of a microorganism, methylamine, isobutylamine, putrescine, cadaverine, histamine, tyramine, phenethylamine and fatty acids.

II. Device

In another embodiment, the present invention provides a device for monitoring an analyte in an environment. The device includes at least one sensor array, wherein the at least one sensor array comprises at least two sensors capable of producing a first response in the presence of a chemical stimulus; a second sensor which is capable of producing a second response in the presence of a physical stimulus; a connector that connects the at least one sensor array and the second sensor to a central processing unit, wherein the central processing unit collects and stores the first and second responses; and an analyzer configured to analyze a plurality of responses wherein the analyzer monitors said analyte in the environment. In a preferred embodiment, the device is a handheld device.

The device of the present invention can be a handheld model such as that disclosed in WO 99/47905, published Sep. 23, 1999, and U.S. patent application Ser. No. 09/518,179, filed Mar. 2, 2000, both incorporated herein by reference, or a desktop model device wherein the sensors array(s) are in close proximity to each other. In certain embodiments, wherein a plurality of arrays are used, the sensors can be separated over larger spatial areas, wherein the sensor arrays are connected via a network, such as a computer local area network, or the Internet.

In one specific embodiment, such as a handheld device, a sensor chamber contains an array of chemical sensors and an infrared sensor array. In this aspect, a light source produces a broad band radiation through a sample path. An analyte source, such as human breath containing alcohol, is introduced in the sensor module. The chemical sensor array responds with a signal, such as an electrical signal.

Figure 3:
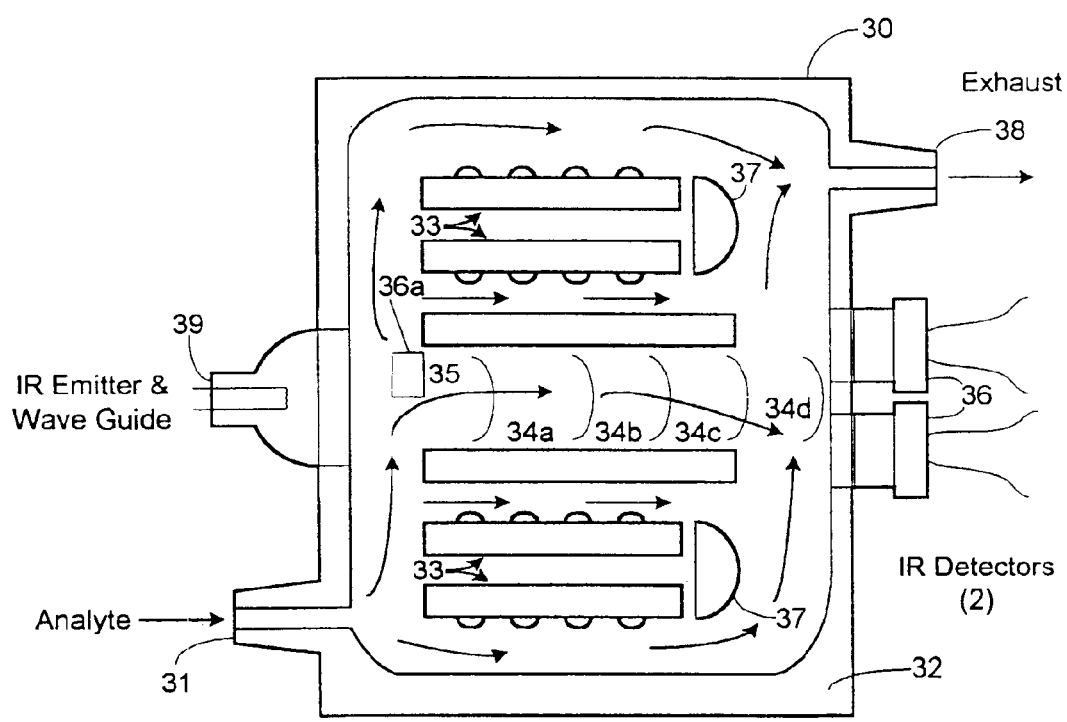
FIG. 3 shows a top sectional view of an embodiment of a sensor module that includes four sensor devices mounted within two sample chambers.

With reference to FIG. 3, the test sample is directed through a sensor module 30 from an inlet port 31, through the sample chamber 32 and to an exhaust port 38. Sensor array devices 33, such as a polymer composite, are arranged such that the test sample moves laterally across the exposed chemically sensitive sensors. Baffles 37 are located at the trailing ends of each sensor array to assist in providing an efficient flow pattern. The IR source 39 is centrally located and enters the sample chamber. IR filter(s) 34a, 34b, 34c, 34d are displaceable in the path of the IR beam. At least one IR sensor 36 is located beyond the filters. Another sensor is located in front of the filter (36a).

In operation, radiation emanating from an IR radiation source 39 enters a measuring chamber 35 disposed within the sample chamber. In certain embodiments, a resonance amplifier is connected to the IR sensors, the resonance amplifier being a narrow-band amplifier that is arranged to be regulable. A filter member and a rectifier are connected to the output of the resonance amplifier. In addition to the first IR sensor beyond the filter(s), a second sensor is arranged in the path of the beam in front of the filter(s) and thus receives the unfiltered radiation emerging directly from the IR source. However, it must not be pushed into the path of the beam since it would otherwise mask the radiation. Preferably, the second detector is arranged in the range of reflection of the filter(s) and receives the unfiltered radiation reflected from the front side of the filter.

Figure 4:
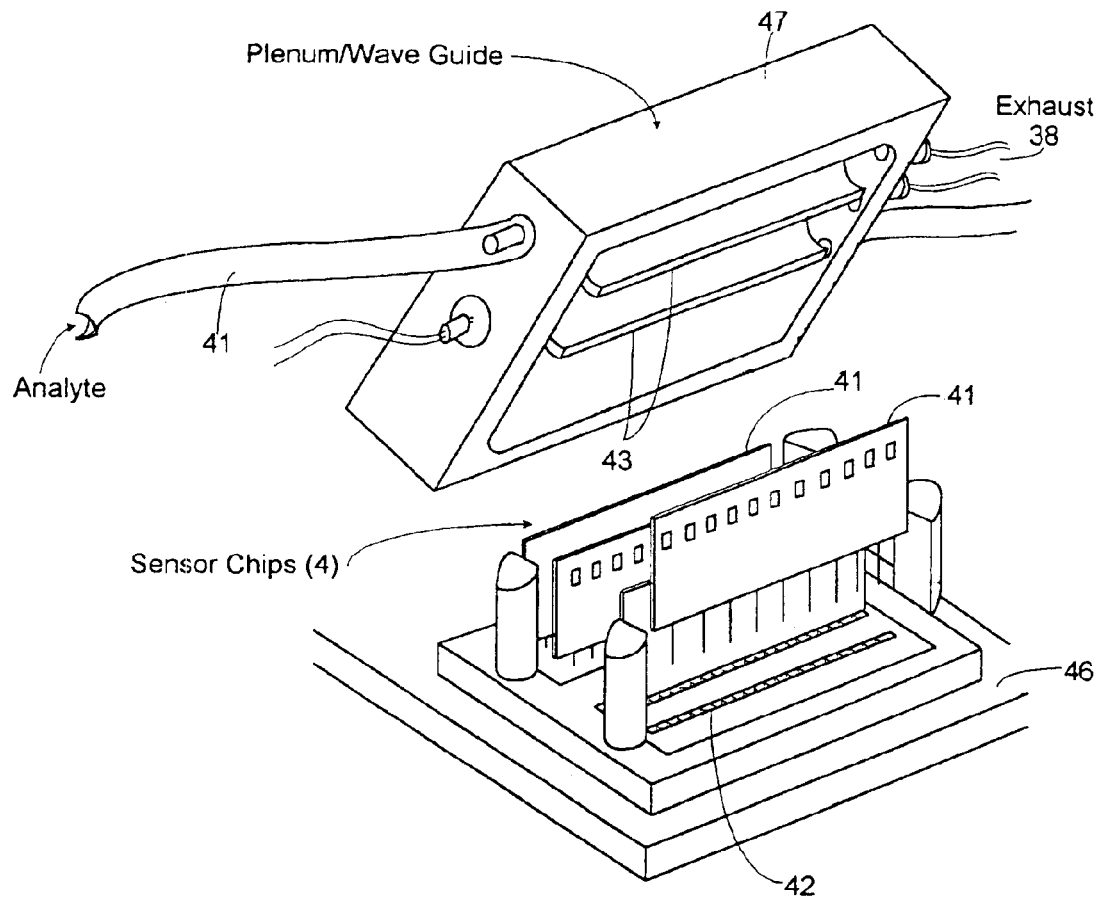
FIG. 4 shows a perspective view of an embodiment of a sensor module that includes four sensor devices mounted within two sample chambers.
Figure 5:
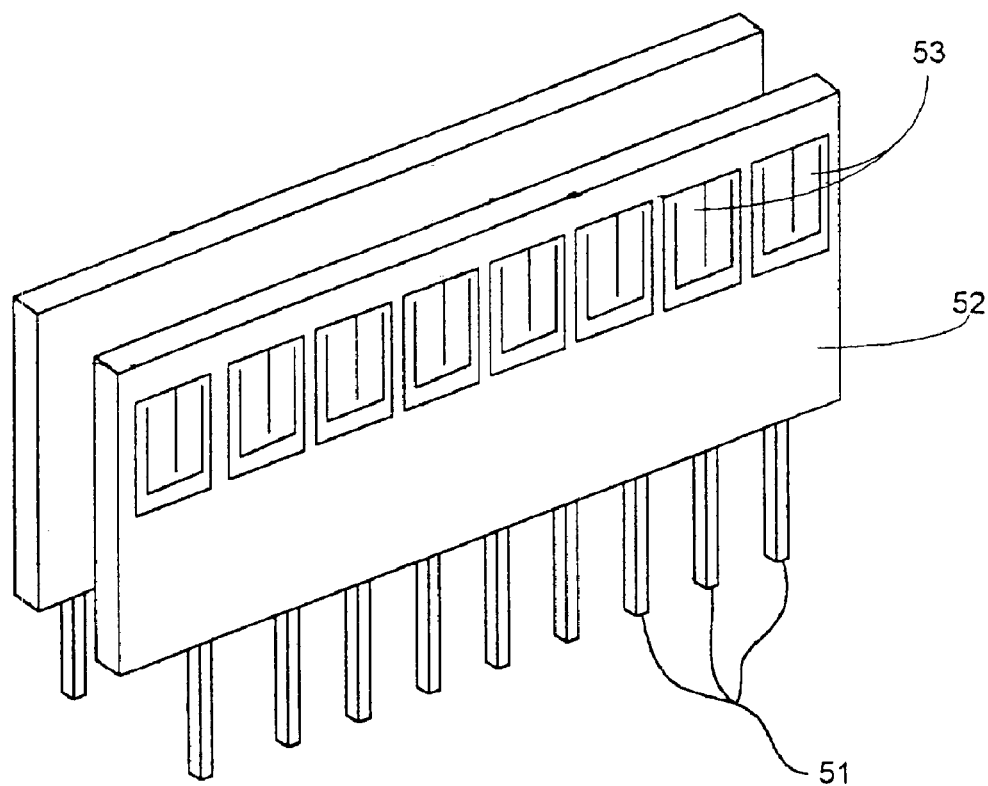
FIG. 5 shows a perspective view of a sensor array device.

FIG. 4 shows a perspective view of an embodiment of a sensor module that includes four sensor devices mounted within two sample chambers 43. In FIG. 4 the sensor module is depicted as being configured for non-removable securement to a printed circuit board (PCB), but which alternatively could be configured as a plug-in module such as sensor module. In a specific embodiment, the sensor module incorporates four plug-in sensor array devices 41, each including eight chemically sensitive sensors 53 (FIG. 5). Sensor module can include greater or fewer number of sensor array devices, and each sensor array device can include greater or fewer number of sensors. The four sensor array devices 41 are mounted vertically in pairs on a board 46. A cover 47 having a pair of elongated recesses is secured over board 46 so as to define two separate sample chambers 43, one for each pair of sensor array devices 41. Sensor array devices 41 are of similar shape and size, and each can be received in any one of the four connectors, or receptacles 42, formed in board 46.

FIG. 5 is a perspective view of one sensor array device 52. In an embodiment, each sensor array device 52 includes an array of eight chemically sensitive sensors 53, each providing a particular characteristic response when exposed to a test sample carrying analytes to be sensed. In another embodiment, the sensors are implemented using chemically sensitive resistors that provide particular resistances when exposed to a test sample. A multi-contact electrical connector 51 is located along the lower edge of sensor array device 52 and is configured for insertion into one of four receptacles 42. Suitable sensor arrays of this kind are disclosed in U.S. Pat. No. 5,575,401, issued in the names of Nathan S. Lewis et al., entitled "Sensor Arrays for Detecting Analytes in Fluids," and incorporated herein by reference. Sensors disclosed in WO 99/27357, published Jun. 6, 1999, are also suitable for use in the present invention. Those of ordinary skill in the art will appreciate that various alternative chemically sensitive sensors or devices could also be used.

In accordance with certain embodiments of the invention, a radiation source in the form of a IR radiation source, located upstream of the radiation inlet, a filter, such as a filter having a pass band at 3.46 $\mu$m, a first IR sensor arranged beyond the filter, a second IR sensor arranged in the path of the beam beyond the radiation source of the sample chamber and in front of the filter, an amplifier connected to the output of the first sensor, a reference voltage source connected to the output of the second sensor, the outputs of the amplifier and the reference voltage source being connected to a differential amplifier.

The IR radiation source, can be a simple incandescent lamp in a quartz bulb. The radiation is split up into two portions beyond the radiation outlet of the sample chamber, one of which portions includes or supplies the measuring signal and the other portion acts as a control variable and a reference variable of the optical state of the measuring chamber. Operations are carried out simultaneously with both portions. Thus, errors do not occur which otherwise occur in arrangements wherein two different sample chambers or as a result of two successive measurements. The signal of the first detector is fed to a resonance amplifier or signal amplifier. The signal of the second detector is fed by way of an amplifier to a reference voltage source and controls the latter. The two voltages, that is the signal voltage and the reference voltage, are subtracted and the difference is amplified in the differential amplifier. The reference voltage source monitors, inter alia, the optical state of the measuring chamber and the radiation source. The voltage supplied by the reference voltage source changes upon a change in the intensity of radiation. Thus, changes at the radiation outlet, not attributable to the analyte content of the vapor are removed from the measurement in that equal voltages appearing in the measuring and control path are subtracted from one another.

Background air is introduced into the sample chamber in order to set up the apparatus. The second IR sensor is then set such that the signals in the two amplifiers are equal and the difference becomes zero. If the vapor containing the analyte is now introduced into the sample chamber, the intensity of the infrared radiation filtered out of the entire range by the filter is reduced by absorption by the analyte molecules, while the visible portion of the radiation reflected on the front face of the filter is not influenced by analyte and does not cause any change in the reference voltage.

Using the Beers-Lambert law set forth below:

$$\phi_e/\phi_o = e^{-mcd}$$

wherein $\phi_e$ is the emerging current from the first IR sensor; $\phi_o$ is the entering current from the second IR sensor, m is a constant of the analyte; d is the path length and c is concentration of the analyte. Using the foregoing equation is possible to calculate the concentration of the analyte of interest.

It has already been mentioned that the second detector is arranged in the path of the beam in front of the filter and thus receives the unfiltered radiation emerging directly from the measuring chamber. However, it must not be pushed into the path of the beam since it would otherwise mask the radiation. Preferably, the second detector is arranged in the range of reflection of the filter and receives the unfiltered radiation reflected from the front side of the filter.

The first array of sensors comprise at least two sensors capable of producing a first response in the presence of a chemical stimulus. The second array of sensors comprises at least two infrared sensors capable of producing a second response, such as in the presence of a physical stimulus; a connector that connects each of the sensors comprising the at least two sensor arrays to a central processing unit that collects and stores the first and the second responses; and an analyzer configured to analyze a plurality of responses from the at least two sensor arrays, wherein the analyzer monitors the analytes in the environment.

Figure 6:
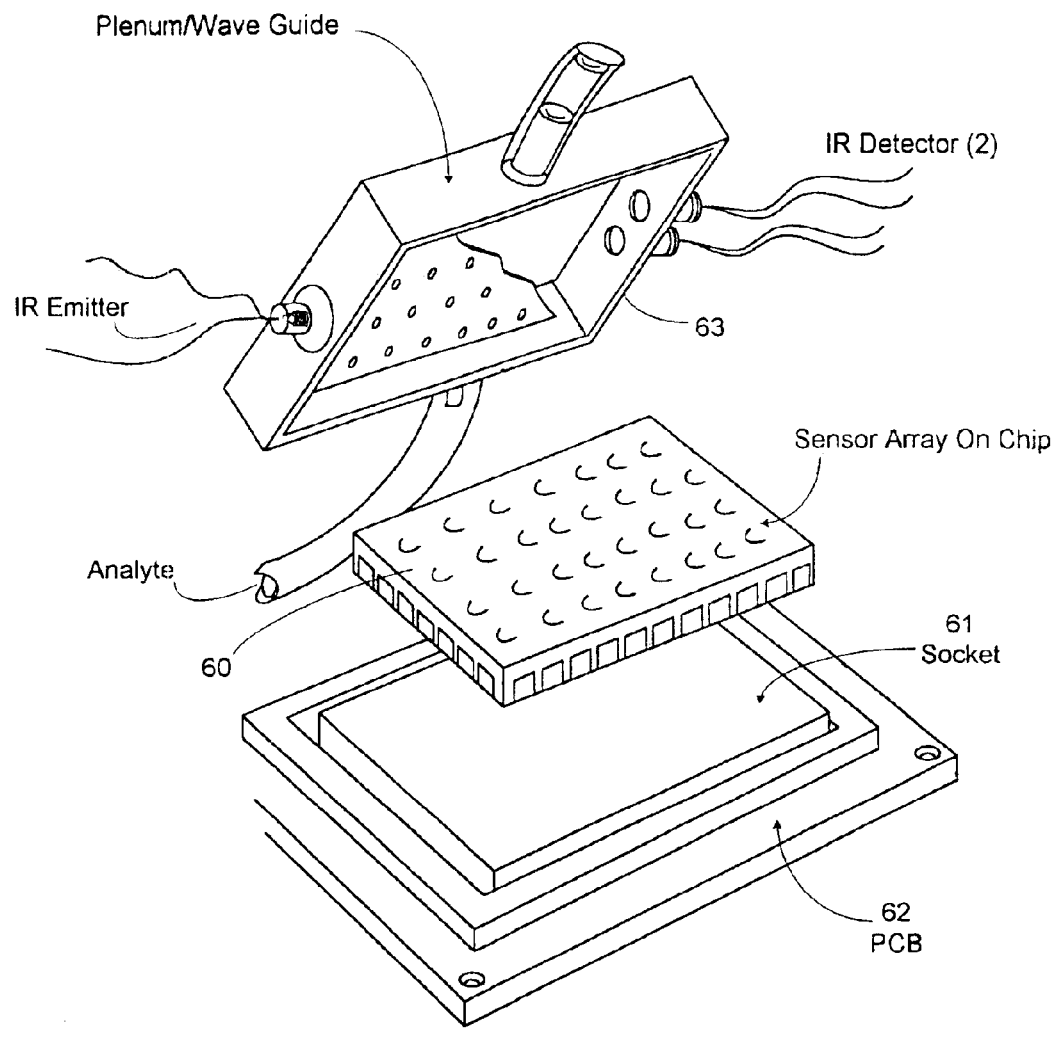
FIG. 6 shows an IR/polymer based sensor.

FIG. 6 shows a perspective view of an embodiment of yet another sensor module that includes a single sensor array device 60. In a specific embodiment, sensor array device 60 includes thirty two chemically sensitive sensors arranged in a two-dimensional grid and is mounted in a generally horizontal orientation on a socket 61. Of course, sensor array device 60 can include greater or fewer number of sensors.

Figure 7:
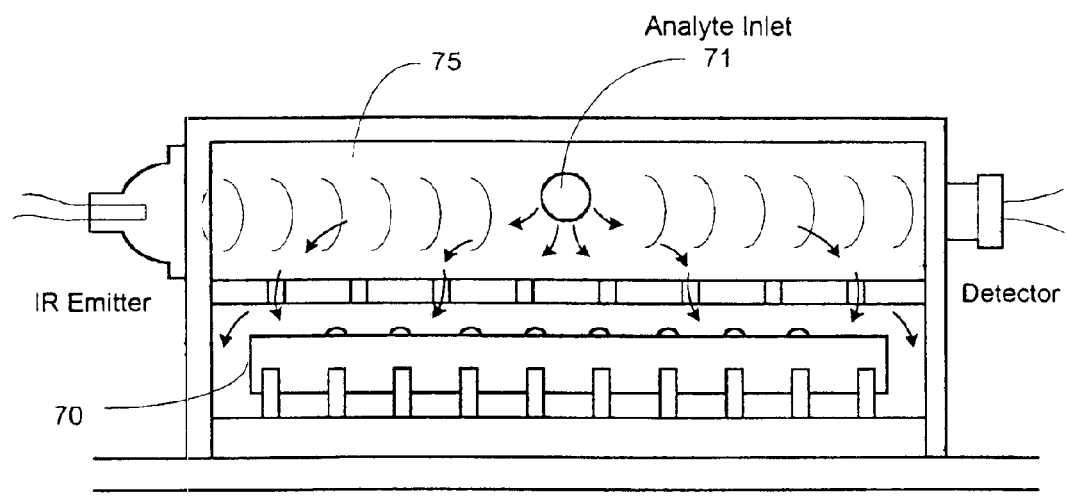
FIG. 7 shows a sectional view of an embodiment of a sensor chamber.

As shown in FIG. 7, the test sample being analyzed is directed from an inlet port 71 to a measuring chamber 75 and from there to where it passes across the chemically sensitive sensors 70. The test sample then exits through an outlet port. Again, it will be appreciated that various alternative chemically sensitive sensors and devices could also be used.

Figure 8:
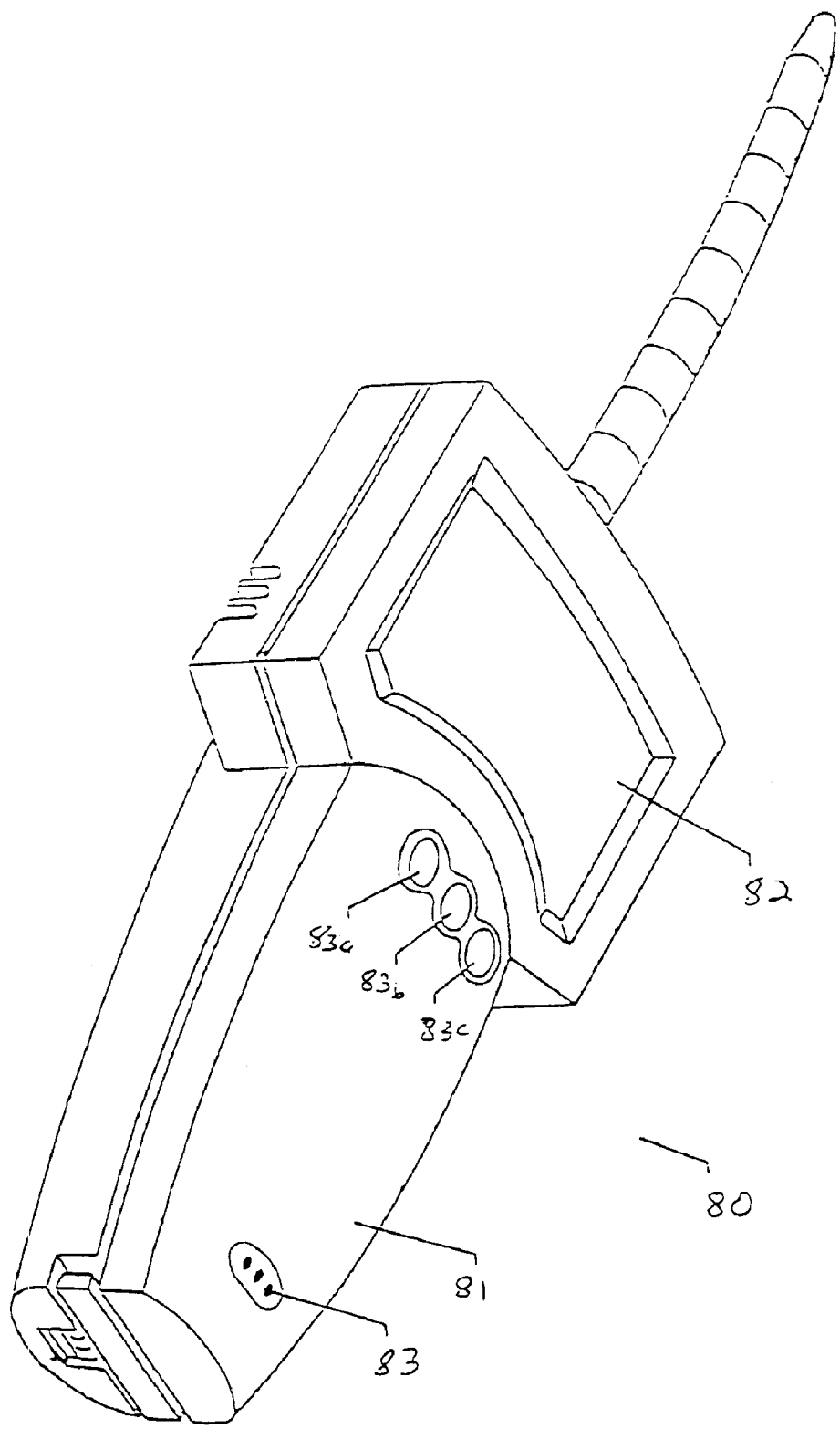
FIG. 8 shows a handheld device of the present invention.

FIG. 8 illustrates a handheld device of the present invention. As illustrated therein, handheld device 80 includes an elongated housing 81 having a lower end sized to be conveniently grasped and supported by the hand of an operator. A display 82 and several push-button control switches 83a through 83c are located on the housing's topside, for convenient viewing and access by the operator. Push-button switches 83 are used to control the device during its various operating modes. Display 82 displays information about such operating modes and the results of the device's sensing.

In certain embodiments, the identification of analytes and the determination of sample concentration can be performed by an "analyzer." (See, U.S. patent application Ser. No. 09/518,179, filed Mar. 2, 2000). As used herein, the analyzer can be a processor, a DSP processor, a specially designed ASIC, or other circuits designed to performed the analysis functions described herein. The analyzer can also be a general-purpose processor executing program codes written to perform the required analysis functions.

In another aspect, the present invention provides sensor devices suitable for fire and smoke detection. In certain instances, the most effective way to detect fire initiation is to look for and detect end products of the oxidation process. These three elemental entities (carbon, oxygen and hydrogen) and three compounds (carbon dioxide, carbon monoxide and water vapor) are invariably involved in the ensuing chemical reactions or combustion of a fire.

In certain preferred aspects, carbon dioxide that is generated abundantly right from the start of the fire can easily be measured accurately using Non-Dispersive Infrared (NDIR) techniques of the present invention. The average ambient carbon dioxide concentration level of about 200 ppm does not hinder the detection of additional fire-induced quantities as long as the carbon dioxide sensor is designed to have such a fine sensitivity.

In accordance with the present invention, radiation from a quasi-blackbody source that is pulsed electrically is conducted through a gas sample chamber to a detector that is equipped with a single pass band filter whose pass band is located at a strong absorption band of carbon dioxide. In the preferred embodiment the absorption band at 4.26 microns is used.

The detector generates an electrical signal related to the intensity of the radiation falling on it. This signal decreases as the concentration of carbon dioxide in the sample chamber increases as the fire develops. An electronic circuit responsive to this signal produces signals representative of the concentration of the carbon dioxide and representative of the rate of change of the concentration. These signals are compared with preset threshold levels and an alarm is generated in accordance with a built-in rule.

III. Sensors

In one embodiment, the multiple sensing device of the present invention contains at least two sensor arrays. In certain aspects, the first array of sensors comprises at least two sensors capable of producing a first response in the presence of a chemical stimulus. Suitable chemical stimuli capable of detection include, but are not limited to, a vapor, a gas, a liquid, a solid, an odor or mixtures thereof.

Suitable sensors for the systems and devices of the present invention comprising the first array of sensors include, but are not limited to, conducting/nonconducting regions sensor, a SAW sensor, a quartz microbalance sensor, a conductive composite sensor, a chemiresitor, a metal oxide gas sensor, an organic gas sensor, a MOSFET, a piezoelectric device, an infrared sensor, a sintered metal oxide sensor, a Pd-gate MOSFET, a metal FET structure, a electrochemical cell, a conducting polymer sensor, a catalytic gas sensor, an organic semiconducting gas sensor, a solid electrolyte gas sensors, and a piezoelectric quartz crystal sensor. It will be apparent to those of skill in the art that the electronic nose array can be comprises of combinations of the foregoing sensors.

In certain embodiments, a second sensor can be a single sensor or an array of sensors capable of producing a second response in the presence of physical stimuli. The physical detection sensors detect physical stimuli. Suitable physical stimuli include, but are not limited to, thermal stimuli, radiation stimuli, mechanical stimuli, pressure, visual, magnetic stimuli, and electrical stimuli.

Thermal sensors can detect stimuli which include, but are not limited to, temperature, heat, heat flow, entropy, heat capacity, etc. Radiation sensors can detect stimuli that include, but are not limited to, gamma rays, X-rays, ultraviolet rays, visible, infrared, microwaves and radio waves. Mechanical sensors can detect stimuli which include, but are not limited to, displacement, velocity, acceleration, force, torque, pressure, mass, flow, acoustic wavelength, and amplitude. Magnetic sensors can detect stimuli that include, but are not limited to, magnetic field, flux, magnetic moment, magnetization, and magnetic permeability. Electrical sensors can detect stimuli which include, but are not limited to, charge, current, voltage, resistance, conductance, capacitance, inductance, dielectric permittivity, polarization and frequency.

In certain embodiments, thermal sensors are suitable for use in the present invention that include, but are not limited to, thermocouples, such as a semiconducting thermocouples, noise thermometry, thermoswitches, thermistors, metal thermoresistors, semiconducting thermoresistors, thermodiodes, thermotransistors, calorimeters, thermometers, indicators, and fiber optics.

In other embodiments, various radiation sensors are suitable for use in the present invention that include, but are not limited to, nuclear radiation microsensors, such as scintillation counters and solid state detectors, ultra-violet, visible and near infrared radiation microsensors, such as photoconductive cells, photodiodes, phototransistors, infrared radiation microsensors, such as photoconductive IR sensors and pyroelectric sensors. Optical sensors also detect visible, near infrared and infrared waves.

In certain other embodiments, various mechanical sensors are suitable for use in the present invention and include, but are not limited to, displacement microsensors, capacitive and inductive displacement sensors, optical displacement sensors, ultrasonic displacement sensors, pyroelectric, velocity and flow microsensors, transistor flow microsensors, acceleration microsensors, piezoresistive microaccelerometers, force, pressure and strain microsensors, and piezoelectric crystal sensors.

In certain other embodiments, various chemical or biochemical sensors are suitable for use in the present invention and include, but are not limited to, metal oxide gas sensors, such as tin oxide gas sensors, organic gas sensors, chemocapacitors, chemoidiodes, such as inorganic Schottky device, metal oxide field effect transistor (MOSFET), piezoelectric devices, ion selective FET for pH sensors, polymeric humidity sensors, electrochemical cell sensors, pellistors gas sensors, piezoelectric or surface acoustical wave sensors, infrared sensors, surface plasmon sensors, and fiber optical sensors.

Various other sensors suitable for use in the present invention include, but are not limited to, sintered metal oxide sensors, phthalocyanine sensors, membranes, Pd-gate MOSFET, electrochemical cells, conducting polymer sensors, lipid coating sensors and metal FET structures. In certain preferred embodiments, the sensors include, but are not limited to, metal oxide sensors such as a Tuguchi gas sensors, catalytic gas sensors, organic semiconducting gas sensors, solid electrolyte gas sensors, piezoelectric quartz crystal sensors, fiber optic probes, a micro-electro-mechanical system device, a micro-opto-electro-mechanical system device and Langmuir-Blodgett films.

In another embodiment, the present invention includes detection using sensors as disclosed in U.S. Pat. No. 5,814,524, which issued to Walt et al., on Sep. 29, 1998. An optical detection and identification system is disclosed therein that includes an optic sensor, an optic sensing apparatus and methodology for detecting and evaluating one or more analytes of interest, either alone or in mixtures. The system is comprised of a supporting member and an array formed of heterogeneous, semi-selective polymer films which function as sensing receptor units and are able to detect a variety of different analytes using spectral recognition patterns. Using this system, it is possible to combine viewing and chemical sensing with imaging fiber chemical sensors.

IV. Sensor Selection

Figure 9:
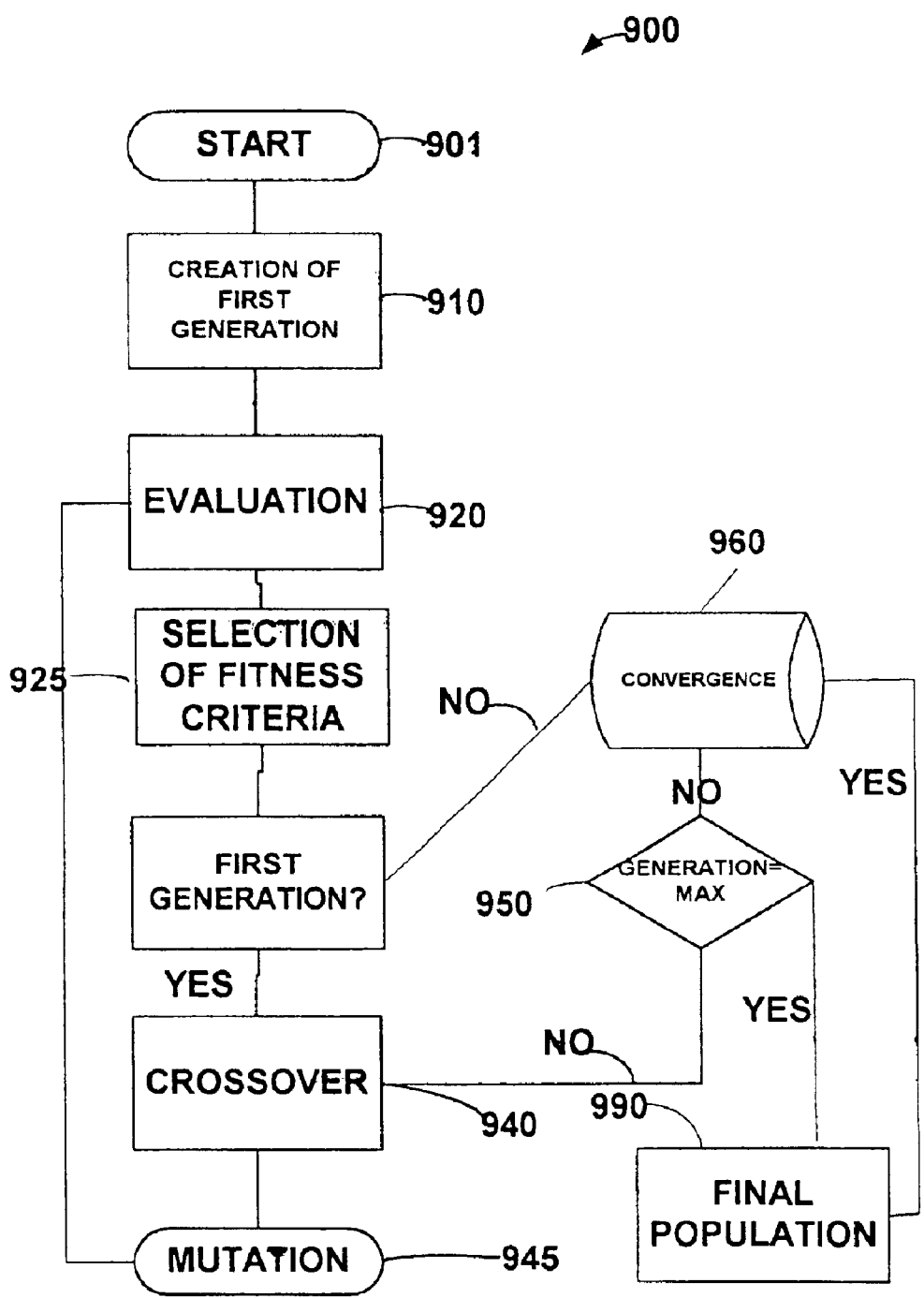
FIG. 9 shows a flow diagram of the present invention.

In certain embodiments, the system of the present invention comprises an optimization of sensor modalities algorithm. FIG. 9 represents a flow diagram of the optimization algorithm whereby the sensor selection is made. This diagram is merely an illustration and should not limit the scope of the claims herein. One of ordinary skill in the art will recognize other variations, modifications, and alternatives.

Among the sensors of various types it is possible that sensors of a certain kind or modality are more suitable for a particular application. The system of the present invention will gather responses from sensors of different types and apply an appropriate sensor selection algorithm to determine optimal sensor types or modalities for a particular use or application. In certain aspects, a genetic algorithm is used.

The genetic algorithm of the present invention can be used for predictive variable selection with classification or regression models.

In step 901, the starting input includes a matrix of predictor variables (sensor responses) and a matrix of predicted variables (categorical or continuous variables). The output is a population 990 that has passed the fitness convergence criteria embodied in the genetic algorithm. The fitness of the final members of the population is provided and members of the final population contain 1's and 0's. As shown below, a 1 means a variable was included, and a 0 means that it was not included. The fitness depends on a variety of selection criteria. Suitable sensor selection criteria include, but are not limited to, the prediction error rate, the type of analyte to be detected, sensor availability, cost, power consumption, environmental conditions, polymer selection, etc. For instance, particular analytes are more responsive to particular polymer types e.g., ammonia and methanol are response to polypyrole. In addition, combustible gas analytes are easily detected with metal oxide sensors.

The genetic algorithm of the present invention aids in the determination of which type of sensor to use in a particular array for a particular application. The selection process can be done during or after the sensing process or it can be an iterative selection process. In certain aspects, the sensors of various modalities, types or kinds are more suitable for a particular application. The system of the present invention will gather responses from sensors of different types and apply appropriate sensor selection algorithms to determine optimal sensor types for a particular application.

In certain aspects, the genetic algorithms are based on principles of natural evolution and selection. A random population of possible models (solutions) 910 or first generation is chosen first. In one embodiment, a possible model is produced in a binary form where 1 indicates inclusion of a sensor variable (or term derived from it) and 0 indicates that a sensor variable has not been included, e.g., members in a population can have the forms:

00111001011101 . . .
11101010011000 . . .

For any model structure, a classification or regression analysis is carried out for evaluation 920 and the prediction error rate is determined on which are based the fitness criteria 925. The models are then ranked based on the fitness criteria. The model forms with the lowest prediction error are allowed to survive and breed. Pairs of these models are randomly selected for breeding using a crossover technique 940. New generations and mutations 945 are thus created. Fitness criteria are again applied. The process continues until the maximum generations are allowed 950 before the algorithm quits and checks the final population 990. The algorithm can also quit when the convergence criteria are reached 960. The output is the final population 990 at either convergence 960 or at maximum generations allowed 950. The variables i.e., sensors, which are present most in the final population, are the ones selected. Thus, by using the genetic algorithm of the present invention, the best sensor for the particular application can be ascertained.

In one embodiment, the extended compact genetic algorithm (ECGA) is used. Based on the analysis using this algorithm, empirical relations for population sizing and convergence time can be derived and are compared with the existing relations. After applying ECGA, an optimal sensor selection is obtained, with improved efficiency of sensor selection capabilities of the system.

Sensor/feature selection can include wavelength selection (Lucasius, C. B.; Beckers, M. L. M.; Kateman, G., *Anal.*

*Chim. Acta* 1994, 286, 135–153 and Vankeerberghen, P.; Smeyers-Verbeke, J.; Leardi, R.; Karr, C. L.; Massart, D. L. *Chemom. Intell. Lab. Syst.* 1995, 28, 73–87.); feature selection (Leardi, R. J. *Chemom.* 1994, 8, 65–79.); and kinetic parameter selection (Hibbert, D. B., *Chemom. Intell. Lab. Syst.* 1993, 19, 319–329.

In another embodiment, the genetic Bayesian optimization algorithm (BOA) with decision graphs is employed (Pelikan, Goldberg, & Sastry, 2000). The BOA provides improved optimization of sensor selection for various applications.

The computer platform used to implement the above embodiment includes Pentium class based computers, Power PC based computers, Digital computers, SunMicrosystems computers, etc.; computer operating systems may include WINDOWS NT, DOS, MacOs, UNIX, VMS, etc.; programming languages may include C, C++, Pascal, JAVA, an object-oriented language, etc. Various modifications of the illustrated embodiments as well as other embodiments of the invention will become apparent to those persons skilled in the art upon reference to this description. A number of the above processes can be separated or combined into hardware, software, or both and the various embodiments described should not be limiting.

V. Analysis

Various analyses suitable for identifying analytes and quantifying concentration include, but are not limited to, principal component analysis, Fischer linear analysis, neural networks, genetic algorithms, fuzzy logic, pattern recognition, and other algorithms. After analysis is completed, the resulting information is displayed on display or transmitted to a host computer.

Many of the algorithms are neural network based algorithms. A neural network has an input layer, processing layers and an output layer. The information in a neural network is distributed throughout the processing layers. The processing layers are made up of nodes that simulate the neurons by its interconnection to their nodes.

In operation, when a neural network is combined with a sensor array, the sensor data is propagated through the networks. In this way, a series of vector matrix multiplications are performed and unknown analytes can be readily identified and determined. The neural network is trained by correcting the false or undesired outputs from a given input. Similar to statistical analysis revealing underlying patterns in a collection of data, neural networks locate consistent patterns in a collection of data, based on predetermined criteria.

Suitable pattern recognition algorithms include, but are not limited to, principal component analysis (PCA), Fisher linear discriminant analysis (FLDA), soft independent modeling of class analogy (SIMCA), K-nearest neighbors (KNN), neural networks, genetic algorithms, fuzzy logic, and other pattern recognition algorithms. In a preferred embodiment, the Fisher linear discriminant analysis (FLDA) and canonical discriminant analysis (CDA) and combinations thereof are used to compare the output signature and the available data from the electronic library. The operating principles of various algorithms suitable for use in the present invention are disclosed (see, Shaffer et al., *Analytica Chimica Acta*, 384, 305–317 (1999)), the teaching of which are incorporated herein by reference.

In certain instances, a statistical metric is used as disclosed in WO 99/61902, published Dec. 2, 1999, and incorporated herein by reference in its entirety for all purposes. A method for distinguishing different odors or vapor is disclosed therein. The method steps include providing a plurality of d sensors in an array, each sensor having different electrical responses to different orders; exposing the sensors to first and second odors; generating first and second sets of data points from each of the sensors, each set corresponding to the first or second odor, each data point being represented by a vector in a d-dimensional space; determining an axis in the d-dimensional space, the axis having the property that projections of the data points onto the axis in the d-dimensional space have optimal separation; and resolving the first odor from the second odor by the separation.

In other embodiments, principal component analysis is used. Principal component analysis (PCA) involves a mathematical technique that transforms a number of correlated variables into a smaller number of uncorrelated variables. The smaller number of uncorrelated variables is known as principal components. The first principal component or eigenvector accounts for as much of the variability in the data as possible, and each succeeding component accounts for as much of the remaining variability as possible. The main objective of PCA is to reduce the dimensionality of the data set and to identify new underlying variables.

In practice, PCA compares the structure of two or more covariance matrices in a hierarchical fashion. For instance, one matrix might be identical to another except that each element of the matrix is multiplied by a single constant. The matrices are thus proportional to one another. More particularly, the matrices share identical eigenvectors (or principal components), but their eigenvalues differ by a proportional constant. Another relationship between matrices is that they share principal components in common, but their eigenvalues differ. The mathematical technique used in PCA is called eigen analysis. The eigenvector associated with the largest eigenvalue has the same direction as the first principal component. The eigenvector associated with the second largest eigenvalue determines the direction of the second principal component. The sum of the eigenvalues equals the trace of the square matrix and the maximum number of eigenvectors equals the number of rows of this matrix. (see, *Advances in Multivariate Statistical Analysis*, p. 31–43, in A. K. Gupta (ed), Reidel, Boston; and Flury, B. (1988) *Common Principal Components and Related Multivariate Models*, Wiley, New York). Commercially available statistical packages and software programs are available for performing principal component analysis (SAS Institute Inc., Cary, N.C., USA or www.sas.com).

It is understood that the embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes in their entirety.

What is claimed is:

1. A method for monitoring the progression of a plume of escaped dangerous gas, said method comprising:

transmitting sensory data from a first sensor array comprising sensors capable of producing a first response in the presence of a chemical stimulus to a remote location;

transmitting physical data from a second sensor array comprising sensors capable of producing a second response in the presence of a physical stimulus to a remote location, wherein said physical data is generated by a sensor of said second sensor array selected from the group consisting of an optical sensor, a mechanical sensor, a radiation sensor, a thermal sensor and combinations thereof; and processing said sensory and physical data at said remote location, wherein said processing comprises analyzing the combination of said first and second responses, thus monitoring the progression of said plume.

2. A method of monitoring an environment surrounding a nuclear facility, said method comprising:

transmitting sensory data from a first sensor array comprising sensors capable of producing a first response in the presence of a chemical stimulus to a remote location;

transmitting physical data from a second sensor array comprising sensors capable of producing a second response in the presence of a physical stimulus to a remote location, wherein said physical data is generated by a sensor of said second sensor array selected from the group consisting of an optical sensor, a mechanical sensor, a radiation sensor, a thermal sensor and combinations thereof; and processing said sensory and physical data at said remote location, wherein said processing comprises analyzing the combination of said first and second responses, thus monitoring said environment.

3. A method of detecting the presence of explosive materials, said method comprising:

transmitting sensory data from a first sensor array comprising sensors capable of producing a first response in the presence of a chemical stimulus to a remote location;

transmitting physical data from a second sensor array comprising sensors capable of producing a second response in the presence of a physical stimulus to a remote location, wherein said physical data is generated by a sensor of said second sensor array selected from the group consisting of an optical sensor, a mechanical sensor, a radiation sensor, a thermal sensor and combinations thereof; and processing said sensory and physical data at said remote location, wherein said processing comprises analyzing the combination of said first and second responses, thus detecting the presence of explosive materials.

4. The method according to claim 1, 2 or 3, further comprising employing a sensor selection algorithm to determine sensors in said first array.

5. The method according to claim 1, 2 or 3, further comprising selecting each sensor of said first sensor array from the group consisting of a bulk conducting polymer film, a semiconducting polymer sensor, a surface acoustic wave device, a fiber optic micromirror, a quartz crystal microbalance, a conducting/nonconducting regions sensor, a dye impregnated polymeric coatings on optical fiber and combinations thereof.

6. The method according to claim 1, 2 or 3, wherein said monitoring includes monitoring a leakage of volatile gases.

7. The method according to claim 1, 2 or 3, wherein said monitoring includes monitoring emission levels.

8. The method according to claim 1, wherein said monitoring includes tracking and the progression of a plume of gas.

9. The method according to claim 1 or 2, wherein said monitoring includes monitoring a perimeter.

10. The method according to claim 1, 2 or 3, wherein said monitoring includes monitoring gases selected from the group consisting of ambient air, combustible gases, natural gas, hazardous leaks, illegal substances, natural gas, smoke, anesthesia gas, sterilization gas, and combinations thereof.

11. The method according to claim 1, 2 or 3, wherein the optical sensor detects visible, near infrared, or infrared radiation, the mechanical sensor detects displacement, velocity, acceleration, force, torque, pressure, mass, flow, acoustic wavelength, or amplitude, the radiation sensor detects gamma rays, X-rays, ultraviolet rays, visible rays, infrared rays, microwaves, or radio waves, and the thermal sensor is a thermocouple.

12. The method according to claim 1, 2 or 3, further comprising taking corrective measures.

13. The method according to claim 12, wherein said taking corrective measures comprises notifying an observer.

14. The method according to claim 13, wherein said notifying comprises providing a visual or an audible alarm.

* * * * *